United States Patent [19]
Williams et al.

[11] Patent Number: 6,140,095
[45] Date of Patent: Oct. 31, 2000

[54] ALKALITOLERANT XYLANASES

[75] Inventors: Diane P. Williams, Hopkinton; Sara Iverson, Lexington; Roberta Lee Farrell, Groton, all of Mass.; Pieter Van Solingen, Naaldwijk, Netherlands; Wilhelmina Theresia Herbes, Noordwijk, Netherlands; Wilhelmus Antonius H. Van Der Kleij, Naaldwijk, Netherlands; Rudolf Franciscus C. Van Beckhoven, Breda, Netherlands; Wilhelmus Johannes Quax, Voorschoten, Netherlands; Margaretha Adriana Herwijer, Amsterdam, Netherlands; Frits Goedegebuur, Vlaardingen, Netherlands; Brian Edward Jones, Leidschendam, Netherlands

[73] Assignee: DSM N.V., Netherlands

[21] Appl. No.: 08/501,126

[22] PCT Filed: Dec. 23, 1994

[86] PCT No.: PCT/EP94/04312

§ 371 Date: Dec. 29, 1995

§ 102(e) Date: Dec. 29, 1995

[87] PCT Pub. No.: WO95/18219

PCT Pub. Date: Jul. 6, 1995

[30] Foreign Application Priority Data

Dec. 24, 1993 [EP] European Pat. Off. .............. 93203694

[51] Int. Cl.[7] .............................. C12N 9/24; C12N 15/56; C12S 3/08
[52] U.S. Cl. .................... 435/200; 435/195; 435/69.1; 435/320.1; 435/252.3; 435/440; 435/278
[58] Field of Search ................................ 435/69.1, 320.1, 435/172.3, 195, 200, 252.3, 278, 440; 536/23.2

[56] References Cited

U.S. PATENT DOCUMENTS 5,677,161  10/1997  Rosenberg et al. ..................... 435/200

FOREIGN PATENT DOCUMENTS

91/10724    7/1991  WIPO .
WO 91/18976 12/1991 WIPO .

OTHER PUBLICATIONS

H. Honda et al., "Purification and Partial Characterization of Alkaline Xylanase from *Escherichia coli* Carrying cCX311", Agric. Biol. Chem. 49(11): 3165–3169, Nov. 1985.

Akiba, T. et al., "Xylanases of Alkalophilic Thermophilic Bacillus," *Methods in Enzymology* (1988) 160:655–659.

Gruninger, H. et al., "A novel, highly thermostable D–xylanase," *Enzyme Microb. Technol.* (1986) 8:309–314.

Gupta, N. et al., "A Thermostable Extracellular Xylanase from Alkalophilic Bacillus sp. NG–27," *Biotechnology Letters* 14(11):1045–1046 (1992).

Nakamura, S. et al., "Thermophilic Alkaline Xylanase from Newly Isolated Alkaliphilic and Thermophilic Bacillus sp. Strain TAR–1," *Biosci. Biotech. Biochem.* (1994) 58(1):78–81.

Hamamoto, T. et al., "Nucleotide Sequence of the Xylanase A Gene of Alkalophilic Bacillus sp. Strain C–125," *Agric. Biol. Chem.* (1987) 51(3):953–955.

Shoham, Y. et al., "Delignification of wood pulp by a thermostable xylanase from *Bacillus stearothermophilus* strain T–6," *Chemical Abstracts* (1994) 120(4):148 Abstract No. 120:33174j.

Bezalel, L. et al., "Characterization and delignification activity of a thermostable α–L–arabinofuranosidase from *Bacillus stearothermophilus,*" *Appl Microbiol Biotechnol* (1993) 40:57–62.

*Primary Examiner*—Rebecca E. Prouty
*Attorney, Agent, or Firm*—Morrison & Foerster LLP

[57] ABSTRACT

The present invention discloses enzymes having xylanase considerable activity at a pH of 9.0 and a temperature of 70° C. The enzymes are obtainable from deposited strains which are related to alkaliphilic Bacilli. The enzymes are suited for use in paper and pulp production processes.

12 Claims, No Drawings

SEQUENCE LISTING (1) GENERAL INFORMATION:

(iii) NUMBER OF SEQUENCES: 20

(2) INFORMATION FOR SEQ ID NO:1:

(i) SEQUENCE CHARACTERISTICS:
       (A) LENGTH: 1191 base pairs
       (B) TYPE: nucleic acid
       (C) STRANDEDNESS: double
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (B) STRAIN: 1-47-3
       (C) INDIVIDUAL ISOLATE: CBS669.93

(ix) FEATURE:
       (A) NAME/KEY: CDS
       (B) LOCATION: 1..1191
       (D) OTHER INFORMATION: /product= "xylanase"

(xi) SEQUENCE DESCRIPTION: SEQ ID NO:1:

```
ATG ATT ACA CTT TTT ACA AAG CCT TTT GTT GCT GGA CTA GCG ATC TCT        48
Met Ile Thr Leu Phe Thr Lys Pro Phe Val Ala Gly Leu Ala Ile Ser
  1               5                  10                  15

TTA TTA GTA GGT AGG GGG CTA GGC AAT GTA GCT GCT CAA GGA GGA            96
Leu Leu Val Gly Arg Gly Leu Gly Asn Val Ala Ala Gln Gly Gly
             20                  25                  30

CCA CCA CAA TCT GGA GTC TTT GGA GAG AAT CAC AAA AGA AAT GAT CAG       144
Pro Pro Gln Ser Gly Val Phe Gly Glu Asn His Lys Arg Asn Asp Gln
         35                  40                  45

CCT TTT GCA TGG CAA GTT GCT TCT CTT TCT GAG CGA TAT CAA GAG CAG       192
Pro Phe Ala Trp Gln Val Ala Ser Leu Ser Glu Arg Tyr Gln Glu Gln
     50                  55                  60

TTT GAT ATT GGA GCT CCG GTT GAG CCC TAT CAA TTA GAA GGA AGA CAA       240
Phe Asp Ile Gly Ala Pro Val Glu Pro Tyr Gln Leu Glu Gly Arg Gln
 65                  70                  75                  80

GCC CAA ATT TTA AAG CAT CAT TAT AAC AGC CTT GTG GCG GAA AAT GCA       288
Ala Gln Ile Leu Lys His His Tyr Asn Ser Leu Val Ala Glu Asn Ala
                 85                  90                  95

ATG AAA CCT GTA TCA CTC CAG CCA AGA GAA GGT GAG TGG AAC TGG GAA       336
Met Lys Pro Val Ser Leu Gln Pro Arg Glu Gly Glu Trp Asn Trp Glu
            100                 105                 110

GGC GCT GAC AAA ATT GTG GAG TTT GCC CGC AAA CAT AAC ATG GAG CTT       384
Gly Ala Asp Lys Ile Val Glu Phe Ala Arg Lys His Asn Met Glu Leu
        115                 120                 125

CGC TTC CAC ACA CTC GTT TGG CAT AGC CAA GTA CCA GAA TGG TTT TTC       432
Arg Phe His Thr Leu Val Trp His Ser Gln Val Pro Glu Trp Phe Phe
    130                 135                 140

ATC GAT GAA AAT GGC AAT CGG ATG GTT GAT GAA ACC GAT CCA GAA AAA       480
Ile Asp Glu Asn Gly Asn Arg Met Val Asp Glu Thr Asp Pro Glu Lys
145                 150                 155                 160

CGT AAA GCG AAT AAA CAA TTG TTA TTG GAG CGA ATG GAA AAC CAT ATT       528
Arg Lys Ala Asn Lys Gln Leu Leu Leu Glu Arg Met Glu Asn His Ile
                165                 170                 175

AAA ACG GTT GTT GAA CGT TAT AAA GAT GAT GTG ACT TCA TGG GAT GTG       576
Lys Thr Val Val Glu Arg Tyr Lys Asp Asp Val Thr Ser Trp Asp Val
```

```
            180                 185                 190
GTG AAT GAA GTT ATT GAT GAT GGC GGG GGC CTC CGT GAA TCA GAA TGG        624
Val Asn Glu Val Ile Asp Asp Gly Gly Gly Leu Arg Glu Ser Glu Trp
        195                 200                 205

TAT CAA ATA ACA GGC ACT GAC TAC ATT AAG GTA GCT TTT GAA ACT GCA        672
Tyr Gln Ile Thr Gly Thr Asp Tyr Ile Lys Val Ala Phe Glu Thr Ala
        210                 215                 220

AGA AAA TAT GGT GGT GAA GAG GCA AAG CTG TAC ATT AAT GAT TAC AAC        720
Arg Lys Tyr Gly Gly Glu Glu Ala Lys Leu Tyr Ile Asn Asp Tyr Asn
225                 230                 235                 240

ACC GAA GTA CCT TCT AAA AGA GAT GAC CTT TAC AAC CTG GTG AAA GAC        768
Thr Glu Val Pro Ser Lys Arg Asp Asp Leu Tyr Asn Leu Val Lys Asp
                245                 250                 255

TTA TTA GAG CAA GGA GTA CCA ATT GAC GGG GTA GGA CAT CAG TCT CAT        816
Leu Leu Glu Gln Gly Val Pro Ile Asp Gly Val Gly His Gln Ser His
                260                 265                 270

ATC CAA ATC GGC TGG CCT TCC ATT GAA GAT ACA AGA GCT TCT TTT GAA        864
Ile Gln Ile Gly Trp Pro Ser Ile Glu Asp Thr Arg Ala Ser Phe Glu
        275                 280                 285

AAG TTT ACG AGT TTA GGA TTA GAC AAC CAA GTA ACT GAA CTA GAC ATG        912
Lys Phe Thr Ser Leu Gly Leu Asp Asn Gln Val Thr Glu Leu Asp Met
        290                 295                 300

AGT CTT TAT GGC TGG CCA CCG ACA GGG GCC TAT ACC TCT TAT GAC GAC        960
Ser Leu Tyr Gly Trp Pro Pro Thr Gly Ala Tyr Thr Ser Tyr Asp Asp
305                 310                 315                 320

ATT CCA GAA GAG CTT TTT CAA GCT CAA GCA GAC CGT TAT GAT CAG TTA       1008
Ile Pro Glu Glu Leu Phe Gln Ala Gln Ala Asp Arg Tyr Asp Gln Leu
                325                 330                 335

TTT GAG TTA TAT GAA GAA TTA AGC GCT ACT ATC AGT AGT GTA ACC TTC       1056
Phe Glu Leu Tyr Glu Glu Leu Ser Ala Thr Ile Ser Ser Val Thr Phe
                340                 345                 350

TGG GGA ATT GCT GAT AAC CAT ACA TGG CTT GAT GAC CGC GCT AGA GAG       1104
Trp Gly Ile Ala Asp Asn His Thr Trp Leu Asp Asp Arg Ala Arg Glu
                355                 360                 365

TAC AAT AAT GGA GTA GGG GTC GAT GCA CCA TTT GTT TTT GAT CAC AAC       1152
Tyr Asn Asn Gly Val Gly Val Asp Ala Pro Phe Val Phe Asp His Asn
        370                 375                 380

TAT CGA GTG AAG CCT GCT TAC TGG AGA ATT ATT GAT TAA                   1191
Tyr Arg Val Lys Pro Ala Tyr Trp Arg Ile Ile Asp  *
385                 390                 395

(2) INFORMATION FOR SEQ ID NO:2:

(i) SEQUENCE CHARACTERISTICS:
            (A) LENGTH:  396 amino acids
            (B) TYPE: amino acid
            (D) TOPOLOGY: linear (ii) MOLECULE TYPE: protein (xi) SEQUENCE DESCRIPTION: SEQ ID NO:2:

Met Ile Thr Leu Phe Thr Lys Pro Phe Val Ala Gly Leu Ala Ile Ser
  1               5                  10                  15

Leu Leu Val Gly Arg Gly Leu Gly Asn Val Ala Ala Ala Gln Gly Gly
                 20                  25                  30

Pro Pro Gln Ser Gly Val Phe Gly Glu Asn His Lys Arg Asn Asp Gln
             35                  40                  45

Pro Phe Ala Trp Gln Val Ala Ser Leu Ser Glu Arg Tyr Gln Glu Gln
         50                  55                  60

Phe Asp Ile Gly Ala Pro Val Glu Pro Tyr Gln Leu Glu Gly Arg Gln
```

```
                  65                  70                  75                  80
Ala Gln Ile Leu Lys His His Tyr Asn Ser Leu Val Ala Glu Asn Ala
                         85                  90                  95

Met Lys Pro Val Ser Leu Gln Pro Arg Glu Gly Glu Trp Asn Trp Glu
                100                 105                 110

Gly Ala Asp Lys Ile Val Glu Phe Ala Arg Lys His Asn Met Glu Leu
                115                 120                 125

Arg Phe His Thr Leu Val Trp His Ser Gln Val Pro Glu Trp Phe Phe
        130                 135                 140

Ile Asp Glu Asn Gly Asn Arg Met Val Asp Glu Thr Asp Pro Glu Lys
145                 150                 155                 160

Arg Lys Ala Asn Lys Gln Leu Leu Glu Arg Met Glu Asn His Ile
                165                 170                 175

Lys Thr Val Val Glu Arg Tyr Lys Asp Asp Val Thr Ser Trp Asp Val
                180                 185                 190

Val Asn Glu Val Ile Asp Asp Gly Gly Leu Arg Glu Ser Glu Trp
        195                 200                 205

Tyr Gln Ile Thr Gly Thr Asp Tyr Ile Lys Val Ala Phe Glu Thr Ala
        210                 215                 220

Arg Lys Tyr Gly Gly Glu Glu Ala Lys Leu Tyr Ile Asn Asp Tyr Asn
225                 230                 235                 240

Thr Glu Val Pro Ser Lys Arg Asp Asp Leu Tyr Asn Leu Val Lys Asp
                245                 250                 255

Leu Leu Glu Gln Gly Val Pro Ile Asp Gly Val Gly His Gln Ser His
                260                 265                 270

Ile Gln Ile Gly Trp Pro Ser Ile Glu Asp Thr Arg Ala Ser Phe Glu
        275                 280                 285

Lys Phe Thr Ser Leu Gly Leu Asp Asn Gln Val Thr Glu Leu Asp Met
        290                 295                 300

Ser Leu Tyr Gly Trp Pro Pro Thr Gly Ala Tyr Thr Ser Tyr Asp Asp
305                 310                 315                 320

Ile Pro Glu Glu Leu Phe Gln Ala Gln Ala Asp Arg Tyr Asp Gln Leu
                325                 330                 335

Phe Glu Leu Tyr Glu Glu Leu Ser Ala Thr Ile Ser Ser Val Thr Phe
            340                 345                 350

Trp Gly Ile Ala Asp Asn His Thr Trp Leu Asp Asp Arg Ala Arg Glu
        355                 360                 365

Tyr Asn Asn Gly Val Gly Val Asp Ala Pro Phe Val Phe Asp His Asn
        370                 375                 380

Tyr Arg Val Lys Pro Ala Tyr Trp Arg Ile Ile Asp
385                 390                 395

(2) INFORMATION FOR SEQ ID NO:3:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: FA (xi) SEQUENCE DESCRIPTION: SEQ ID NO:3:
```

```
CACACKCTKG TKTGGCA                                              17

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
         (C) INDIVIDUAL ISOLATE: FB (xi) SEQUENCE DESCRIPTION: SEQ ID NO:4:

CATACKTTKG TTTGGCA                                              17

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
         (C) INDIVIDUAL ISOLATE: FR (xi) SEQUENCE DESCRIPTION: SEQ ID NO:5:

TMGTTKACMA CRTCCCA                                              17

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
         (C) INDIVIDUAL ISOLATE: GAF (xi) SEQUENCE DESCRIPTION: SEQ ID NO:6:

GARTAYTAYA THGTNGA                                              17

(2) INFORMATION FOR SEQ ID NO:7:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
         (C) INDIVIDUAL ISOLATE: GAR
```

```
    (xi) SEQUENCE DESCRIPTION: SEQ ID NO:7:

CKNACNGACC ARTA                                                        14

(2) INFORMATION FOR SEQ ID NO:8:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: GBF (xi) SEQUENCE DESCRIPTION: SEQ ID NO:8:

GARTAYTAYG TNGTNGA                                                     17

(2) INFORMATION FOR SEQ ID NO:9:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: GBR (xi) SEQUENCE DESCRIPTION: SEQ ID NO:9:

CKNACRCTCC ARTA                                                        14

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (C) INDIVIDUAL ISOLATE: GCR (xi) SEQUENCE DESCRIPTION: SEQ ID NO:10:

CCRCTRCTKT GRTANCCYTC                                                  20

(2) INFORMATION FOR SEQ ID NO:11:

(i) SEQUENCE CHARACTERISTICS:
        (A) LENGTH: 142 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO
```

(vi) ORIGINAL SOURCE:
            (B) STRAIN: 1-43-3
            (C) INDIVIDUAL ISOLATE: CBS672.93

(xi) SEQUENCE DESCRIPTION: SEQ ID NO:11:

CATAGCCAAG TACCTGAATG GTTTTTCATC GATAAAGACG GTAATCGTAT GGTAGATGAA      60

ACAAATCCAG CGAAACGTGA GGCTAATAAA CAGCTTTTAT TAGAGCGGAT GGAAACACAT     120

ATCAAAACGG TTGTGGAACG TT                                              142

(2) INFORMATION FOR SEQ ID NO:12:

(i) SEQUENCE CHARACTERISTICS:
           (A) LENGTH: 194 base pairs
           (B) TYPE: nucleic acid
           (C) STRANDEDNESS: double
           (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (B) STRAIN: 1-47-3
            (C) INDIVIDUAL ISOLATE: CBS669.93

(xi) SEQUENCE DESCRIPTION: SEQ ID NO:12:

CACACGCTGG TTTGGCATAG CCAAGTACCA GAATGGTTTT TCATCGATGA AAATGGCAAT      60

CGGATGGTTG ATGAAACCGA TCCAGAAAAA CGTAAAGCGA ATAAACAATT GTTATTGGAG     120

CGAATGGAAA ACCATATTAA AACGGTTGTT GAACGTTATA AAGATGATGT GACTTCATGG     180

GACGTGGTAA ACGA                                                       194

(2) INFORMATION FOR SEQ ID NO:13:

(i) SEQUENCE CHARACTERISTICS:
           (A) LENGTH: 194 base pairs
           (B) TYPE: nucleic acid
           (C) STRANDEDNESS: double
           (D) TOPOLOGY: linear (ii) MOLECULE TYPE: DNA (genomic)

(iii) HYPOTHETICAL: NO (iv) ANTI-SENSE: NO (vi) ORIGINAL SOURCE:
            (B) STRAIN: 2-26-2
            (C) INDIVIDUAL ISOLATE: CBS673.93

(xi) SEQUENCE DESCRIPTION: SEQ ID NO:13:

CACACGCTGG TTTGGCACAG CCAAGTACCA GAATGGTTTT TCATCGATGA AGACGGCAAT      60

CGGATGGTGG ATGAAACAGA CCCAGATAAA CGTGAAGCGA ATAAACAGCT GTTATTGGAG     120

CGCATGGAAA ACCATATTAA AACGGTTGTT GAACGTTATA AAGATGATGT GACTTCATGG     180

GACGTGGTCA ACGA                                                       194

(2) INFORMATION FOR SEQ ID NO:14:

(i) SEQUENCE CHARACTERISTICS:
           (A) LENGTH: 194 base pairs
           (B) TYPE: nucleic acid
           (C) STRANDEDNESS: double
           (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (B) STRAIN: 2-m-1
             (C) INDIVIDUAL ISOLATE: CBS667.93

(xi) SEQUENCE DESCRIPTION: SEQ ID NO:14:

CACACTCTTG TTTGGCATAG CCAAGTACCA GAATGGTTTT TCATCGATGA AAATGGCAAT     60

CGGATGGTTG ATGAAACCGA TCCAGAAAAA CGTAAAGCGA ATAAACAATT GTTATTGGAG    120

CGAATGGAAA ACCATATTAA AACGGTTGTT GAACGTTATA AAGATGATGT GACTTCATGG    180

GACGTGGTAA ACGA                                                      194

(2) INFORMATION FOR SEQ ID NO:15:

(i) SEQUENCE CHARACTERISTICS:
            (A) LENGTH: 164 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (B) STRAIN: 1-25-2
             (C) INDIVIDUAL ISOLATE: CBS671.93

(xi) SEQUENCE DESCRIPTION: SEQ ID NO:15:

GAATATTATA TTGTCGACAG TTGGGGCAAC TGGCGTCCAC CAGGAGCAAC GCCTAAGGGA     60

ACCATCACTG TTGATGGAGG AACATATGAT ATCTATGAAA CTCTTAGAGT CAATCAGCCC    120

TCCATTAAGG GGATTGCCAC ATTTAAACAA TATTGGAGCG TCCG                     164

(2) INFORMATION FOR SEQ ID NO:16:

(i) SEQUENCE CHARACTERISTICS:
            (A) LENGTH: 164 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (B) STRAIN: 1-43-3
             (C) INDIVIDUAL ISOLATE: CBS672.93

(xi) SEQUENCE DESCRIPTION: SEQ ID NO:16:

GAATATTATA TTGTCGACAG TTGGGGCAAC TGGCGTCCAC CAGGAGCAAC GCCTAAGGGA     60

ACCATCACTG TTGATGGAGG AACATATGAT ATCTATGAAA CTCTTAGAGT CAATCAGCCC    120

TCCATTAAGG GGATTGCCAC ATTTAAACAA TATTGGAGCG TCCG                     164

(2) INFORMATION FOR SEQ ID NO:17:

(i) SEQUENCE CHARACTERISTICS:
            (A) LENGTH: 164 base pairs (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: 1-43-3
        (C) INDIVIDUAL ISOLATE: CBS672.93

(xi) SEQUENCE DESCRIPTION: SEQ ID NO:17:

```
GAATATTACA TCGTTGATAG CTGGGGAAGC TGGCGTCCAC CAGGAGCTAA CGCAAAAGGA      60

ACGATTACTG TTGACGGTGG TGTTTACGAT ATTTATGAAA CAACTCGAGT TAACCAACCT     120

TCCATTATTG GAGATGCGAC TTTCCAACAG TACTGGAGTG TGCG                     164
```

(2) INFORMATION FOR SEQ ID NO:18:

(i) SEQUENCE CHARACTERISTICS:
        (A) LENGTH: 744 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (B) STRAIN: 1-43-3
        (C) INDIVIDUAL ISOLATE: CBS672.93

(ix) FEATURE:
        (A) NAME/KEY: CDS
        (B) LOCATION: 1..744
        (D) OTHER INFORMATION: /product= "xylanase"

(xi) SEQUENCE DESCRIPTION: SEQ ID NO:18:

```
ATG AGC CAA AAG AAA TTG ACG TTG ATT AAC CTT TTT AGT TTG TTT GCA        48
Met Ser Gln Lys Lys Leu Thr Leu Ile Asn Leu Phe Ser Leu Phe Ala
        400             405             410

CTA ACC TTA CCT GCA AGA ATA AGT CAG GCA CAA ATC GTC ACC GAC AAT        96
Leu Thr Leu Pro Ala Arg Ile Ser Gln Ala Gln Ile Val Thr Asp Asn
    415             420             425

TCC ATT GCC ACC CGC GGT GGT TAT GAT TAT GAA TTT TGG AAA GAT AGC       144
Ser Ile Ala Thr Arg Gly Gly Tyr Asp Tyr Glu Phe Trp Lys Asp Ser
430             435             440             445

GGT GGC TCT GGG ACA ATG ATT CTC AAT CAT GGC GGT ACG TTC AGT GCC       192
Gly Gly Ser Gly Thr Met Ile Leu Asn His Gly Gly Thr Phe Ser Ala
            450             455             460

CAA TGG AAT AAT GTT AAC AAT ATA TTA TTC CGT AAA GGT AAA AAA TTC       240
Gln Trp Asn Asn Val Asn Asn Ile Leu Phe Arg Lys Gly Lys Lys Phe
            465             470             475

AAT GAA ACA CAA ACA CAC CAA CAA GTT GGT AAC ATG TCC ATA AAC TAT       288
Asn Glu Thr Gln Thr His Gln Gln Val Gly Asn Met Ser Ile Asn Tyr
            480             485             490

GGC GCA AAC TTC CAG CCA AAC GGT AAT GCG TAT TTA TGC GTC TAT GGT       336
Gly Ala Asn Phe Gln Pro Asn Gly Asn Ala Tyr Leu Cys Val Tyr Gly
    495             500             505

TGG ACT GTT GAC CCT CTT GTT GAA TAT TAT ATT GTC GAC AGT TGG GGC       384
Trp Thr Val Asp Pro Leu Val Glu Tyr Tyr Ile Val Asp Ser Trp Gly
510             515             520             525
```

```
AAC TGG CGT CCA CCA GGA GCA ACG CCT AAG GGA ACC ATC ACT GTT GAT      432
Asn Trp Arg Pro Pro Gly Ala Thr Pro Lys Gly Thr Ile Thr Val Asp
                530                 535                 540

GGA GGA ACA TAT GAT ATC TAT GAA ACT CTT AGA GTC AAT CAG CCC TCC      480
Gly Gly Thr Tyr Asp Ile Tyr Glu Thr Leu Arg Val Asn Gln Pro Ser
                545                 550                 555

ATT AAG GGG ATT GCC ACA TTT AAA CAA TAT TGG AGT GTC CGA AGA TCG      528
Ile Lys Gly Ile Ala Thr Phe Lys Gln Tyr Trp Ser Val Arg Arg Ser
            560                 565                 570

AAA CGC ACG AGT GGC ACA ATT TCT GTC AGC AAC CAC TTT AGA GCG TGG      576
Lys Arg Thr Ser Gly Thr Ile Ser Val Ser Asn His Phe Arg Ala Trp
            575                 580                 585

GAA AAC TTA GGG ATG AAC ATG GGG AAA ATG TAT GAA GTC GCG CTT ACT      624
Glu Asn Leu Gly Met Asn Met Gly Lys Met Tyr Glu Val Ala Leu Thr
590                 595                 600                 605

GTA GAA GGC TAT CAA AGT AGC GGA AGT GCT AAT GTA TAT AGC AAT ACA      672
Val Glu Gly Tyr Gln Ser Ser Gly Ser Ala Asn Val Tyr Ser Asn Thr
                610                 615                 620

CTA AGA ATT AAC GGA AAC CCT CTC TCA ACT ATT AGT AAT AAC GAG AGC      720
Leu Arg Ile Asn Gly Asn Pro Leu Ser Thr Ile Ser Asn Asn Glu Ser
                625                 630                 635

ATA ACT CTA GAT AAA AAC AAT TAG                                      744
Ile Thr Leu Asp Lys Asn Asn  *
            640                 645

(2) INFORMATION FOR SEQ ID NO:19:

(i) SEQUENCE CHARACTERISTICS:
        (A) LENGTH: 247 amino acids
        (B) TYPE: amino acid
        (D) TOPOLOGY: linear (ii) MOLECULE TYPE: protein (xi) SEQUENCE DESCRIPTION: SEQ ID NO:19:

Met Ser Gln Lys Lys Leu Thr Leu Ile Asn Leu Phe Ser Leu Phe Ala
 1               5                  10                  15

Leu Thr Leu Pro Ala Arg Ile Ser Gln Ala Gln Ile Val Thr Asp Asn
                20                  25                  30

Ser Ile Ala Thr Arg Gly Gly Tyr Asp Tyr Glu Phe Trp Lys Asp Ser
            35                  40                  45

Gly Gly Ser Gly Thr Met Ile Leu Asn His Gly Thr Phe Ser Ala
        50                  55                  60

Gln Trp Asn Asn Val Asn Asn Ile Leu Phe Arg Lys Gly Lys Phe
65                  70                  75                  80

Asn Glu Thr Gln Thr His Gln Val Gly Asn Met Ser Ile Asn Tyr
                85                  90                  95

Gly Ala Asn Phe Gln Pro Asn Gly Asn Ala Tyr Leu Cys Val Tyr Gly
            100                 105                 110

Trp Thr Val Asp Pro Leu Val Glu Tyr Tyr Ile Val Asp Ser Trp Gly
            115                 120                 125

Asn Trp Arg Pro Pro Gly Ala Thr Pro Lys Gly Thr Ile Thr Val Asp
            130                 135                 140

Gly Gly Thr Tyr Asp Ile Tyr Glu Thr Leu Arg Val Asn Gln Pro Ser
145                 150                 155                 160

Ile Lys Gly Ile Ala Thr Phe Lys Gln Tyr Trp Ser Val Arg Arg Ser
                165                 170                 175

Lys Arg Thr Ser Gly Thr Ile Ser Val Ser Asn His Phe Arg Ala Trp
```

```
                180             185             190
        Glu Asn Leu Gly Met Asn Met Gly Lys Met Tyr Glu Val Ala Leu Thr
                    195             200             205

Val Glu Gly Tyr Gln Ser Ser Gly Ser Ala Asn Val Tyr Ser Asn Thr
            210             215             220

Leu Arg Ile Asn Gly Asn Pro Leu Ser Thr Ile Ser Asn Asn Glu Ser
        225             230             235             240

Ile Thr Leu Asp Lys Asn Asn
                        245

(2) INFORMATION FOR SEQ ID NO:20:

(i) SEQUENCE CHARACTERISTICS:
            (A) LENGTH: 1521 base pairs
            (B) TYPE: nucleic acid
            (C) STRANDEDNESS: double
            (D) TOPOLOGY: linear (ii) MOLECULE TYPE: DNA (genomic)

(iii) HYPOTHETICAL: NO (vi) ORIGINAL SOURCE:
            (A) ORGANISM: Bacillus sp.
            (C) INDIVIDUAL ISOLATE: DSM 8721

(xi) SEQUENCE DESCRIPTION: SEQ ID NO:20:

GACGAACGCT GGCGGCGTGC CTAATACATG CAAGTCGAGC GCAGGAAGCC GGCGGATCCC      60

TTCGGGGTGA ANCCGGTGGA ATGAGCGGCG GACGGGTGAG TAACACGTGG GCAACCTACC    120

TTGTAGACTG GGATAACTCC GGGAAACCGG GGCTAATACC GGATGATCAT TTGGATCGCA    180

TGATCCGAAT GTAAAAGTGG GGATTTATCC TCACACTGCA AGATGGGCCC GCGGCGCATT    240

AGCTAGTTGG TAAGGTAATG GCTTACCAAG GCGACGATGC GTAGCCGACC TGAGAGGGTG    300

ATCGGCCACA CTGGAACTGA GACACGGTCC AGACTCCTAC GGGAGGCAGC AGTAGGGAAT    360

CATCCGCAAT GGGCGAAAGC CTGACGGTGC AACGCCGCGT GAACGATGAA GGTTTTCGGA    420

TCGTAAAGTT CTGTTATGAG GGAAGAACAA GTGCCGTTCG AATAGGTCGG CACCTTGACG    480

GTACCTCACG AGAAAGCCCC GGCTAACTAC GTGCCAGCAG CCGCGGTAAT ACGTAGGGGG    540

CAAGCGTTGT CCGGAATTAT TGGGCGTAAA GCGCGCGCAG GCGGTCTCTT AAGTCTGATG    600

TGAAAGCCCA CGGCTCAACC GTGGAGGGTC ATTGGAAACT GGGGGACTTG AGTGTAGGAG    660

AGGAAAGTGG AATTCCACGT GTAGCGGTGA AATGCGTAGA TATGTGGAGG AACACCAGTG    720

GCGAAGGCGA CTTTCTGGCC TACAACTGAC GCTGAGGCGC GAAAGCGTGG GGAGCAAACA    780

GGATTAGATA CCCTGGTAGT CCACGCCGTA AACGATGAGT GCTAGGTGTT AGGGGTTTCG    840

ATACCCTTAG TGCCGAAGTT AACACATTAA GCACTCCGCC TGGGGAGTAC GGCCGCAAGG    900

CTGAAACTCA AAGGAATTGA CGGGGGCCCG CACAAGCAGT GGAGCATGTG GTTTAATTCG    960

AAGCAACGCG AAGAACCTTA CCAGGTCTTG ACATCCTCTG ACACCTCTGG AGACAGAGCG   1020

TTCCCCTTCG GGGGACAGAG TGACAGGTGG TGCATGGTTG TCGTCAGCTC GTGTCGTGAG   1080

ATGTTGGGTT AAGTCCCGCA ACGAGCGCAA CCCTTGATCT TAGTTGCCAG CATTCAGTTG   1140

GGCACTCTAA GGTGACTGCC GGTGATAAAC CGGAGGAAGG TGGGGATGAC GTCAAATCAT   1200

CATGCCCCTT ATGACCTGGG CTACACACGT GCTACAATGG ATGGTACAAA GGGCAGCGAG   1260

ACCGCGAGGT TAAGCGAATC CCATAAAGCC ATTCTCAGTT CGGATTGCAG GCTGCAACTC   1320

GCCTGCATGA AGCCGGAATT GCTAGTAATC GCGGATCAGC ATGCCGCGGT GAATACGTTC   1380
```

-continued

| | | | | |
|---|---|---|---|---|
| CCGGGTCTTG | TACACACCGC | CCGTCACACC | ACGAGAGTTT | GTAACACCCG AAGTCGGTGC | 1440 |
| GGTAACCTTT | TGGAGCCAGC | CGNCGAAGGT | GGGACAGATG | ATTGGGGTGA AGTCGTAACA | 1500 |
| AGGTATCCCT | ACCGGAAGGT | G | | | 1521 |

ALKALITOLERANT XYLANASES

TECHNICAL FIELD

The present invention relates to novel microorganisms and to novel enzymes. More specifically the enzymes are alkalitolerant xylanases. These xylanases are obtainable from gram-positive, alkalitolerant microorganisms. The xylanases are applicable under conditions used in the paper and pulp industry i.e. pH=9 and T=70° C.

BACKGROUND OF THE INVENTION

Xylan is a component of plant hemicellulose. Xylan consists of 1,4-glycosidically linked β-D-xylose. Usually xylans have side chains containing xylose and other pentoses, hexoses and uronic acids.

In the paper production process the bleaching of pulp is an important step. Schematically the steps used in the pulp treatment in paper and pulp industry is performed as follows:

Pulp is treated at pH 10–12 at 80° C. to remove most of the lignin in the so-called oxygen delignifying step. The remaining pulp contains 2–5% of lignin. This lignin gives the pulp the brown color. Subsequently, the pulp is bleached in a multistage bleaching process. In this bleaching chemicals such as chlorine, chlorine dioxide, hydrogenperoxide and/or ozone are used to obtain a pulp for high quality paper.

Chlorine and chlorine-containing chemicals are often used to remove lignin, which is responsible for the brownish color of the pulp. Use of the indicated chemicals leads to the formation of dioxin and other chlorinated organic compounds. These compounds form a threat to the environment and there is a growing tendency to omit the use of chemicals giving rise to similar waste products.

This has prompted a tendency to develop chlorine-free processes; total chlorine free (TCF) and elementary chlorine-free (ECF). In these processes hydrogen peroxide or ozone is used for bleaching.

It has been found that the introduction of an enzymatic step in the paper and pulp preparation process has several advantages.

Xylanases have been found to be very useful in the paper and pulp processing. Xylanases have been reported to increase the extractability of lignins from the pulp. Xylanases are mostly used after the oxygen delignifying step. Xylanases cleave the hemicellulose chain linking the lignin to the cellulose chain. After xylanase treatment the lignin is more easily removed in the subsequent steps.
Therefore the use of xylanases leads to a reduction of the consumption of active chlorine in prebleaching of 25–30%. This reduction of chlorine does not afflict the quality parameters of the resulting paper (Viikari et al. 1986. Proc. of the third Int. Conf. Biotechnology in Pulp and Paper Ind., Stockholm, p.67–69 and Bajpai and Bajpai. 1992. Process Biochemistry. 27: 319–325).

The xylanase treatment also reduces the need for other chemicals in the bleaching process.

The use of xylanases from fungal sources in bleaching of kraft pulp has been reported. The pH and temperature optima of these enzymes are: pH=3–5 and T=30–50° C. These values are not ideal for the use in the bleaching process where the prevailing conditions are pH≧9 and temperature ≧70° C.

Xylanases from bacterial origin, with higher pH and/or temperature optima have also been reported for use in the bleaching process. Some of these are the following:
*Bacillus pumilus* (pH=7–9, T=40° C., Nissen et al., 1992. Progress in Biotechnology 7: 325–337), *Dictyoglomus thermophilum* (pH=6–8, T=70° C., European patent application EP 0 511 933), *B.stearothermophilus* T-6 (pH=9.0, T=65° C., Shoham, Y. et al. (1992) Biodegradation 3, 207–18), *B.stearothermophilus* (pH=9, T=50° C., WO 91/18976) and *Thermoanaerobacter ethanolicus* (68° C., Deblois and Wiegel. 1992. Progress in Biotechnology 7: 487–490).

Even though most of the above cited xylanases show activity at pH≧9 and temperature >70° C., their effectiveness under industrial application conditions (i.e. during the bleaching of pulp), in terms of e.g. increased brightness of the pulp is only limited and can vary significantly (see e.g. WO 91/18976, highest increase in pulp brightness at pH 9 and 50° C. is only 0.5% ISO brightness).

SUMMARY OF THE INVENTION

The present invention relates to xylanases having considerable activity at pH 9.0 and at a temperature of 70° C., and which is characterized in that the xylanase is obtainable from a microorganism of which the 16S ribosomal DNA sequence shares more than 92% identity with the 16S ribosomal DNA sequence of strain DSM 8721 as listed in SEQ ID NO 20.

The present invention also relates to xylanases having considerable activity at pH 9.0 and at a temperature of 70° C., and characterized in that the xylanase is obtainable from a microorganism selected from the group consisting of the strains deposited under the following deposition numbers: CBS 666.93, 667.93, 669.93, and 673.93.

The present invention further relates to xylanases having considerable activity at pH 9.0 and a temperature of 70° C. further characterized in that the xylanase produces an increase in % ISO brightness of soft-wood pulp over non-enzymatically treated pulp of at least 1.0, preferably an increase in % ISO brightness of soft-wood pulp between 1.5 and 5.0, in an ECF pulp bleaching process wherein the enzyme treatment of the pulp is carried out at a pH of 9.0 at a temperature of 65° C.

The present invention also relates to xylanases having considerable activity at pH 9.0 and a temperature of 70° C. further characterized in that the xylanase produces an increase in % ISO brightness of soft-wood pulp over non-enzymatically treated pulp of at least 1.0, preferably an increase in % ISO brightness of hard-wood pulp between 1.2 and 3.0, in an ECF pulp bleaching process wherein the enzyme treatment of the pulp is carried out at a pH of 9.0 at a temperature of 65° C.

DETAILED DESCRIPTION OF THE INVENTION

The present invention relates to microorganisms which have been isolated from soil and water samples collected in the environment of alkaline soda lakes in Kenya, East-Africa. These microorganisms have been characterized as being alkaliphilic, Gram-positive and belonging to the genus Bacillus (see below).

The microorganisms have subsequently been screened using a xylan-agar diffusion assay. Strains which showed a clearing zone in this test were isolated as potential xylanase producing strains.

The strains were grown at pH 10, and T=45° C. After centrifugation the culture broth was tested for xylanase activity in an assay at pH=9 and T=80° C. (Example 2).

Eight different strains were found to produce xylanase activity under the indicated conditions. These microorganisms have been deposited at the Centraal Bureau voor de Schimmelcultures in Baarn, the Netherlands under deposition number CBS 666.93, 667.93, 668.93, 669.93, 670.93, 671.93, 672.93, 673.93.

Most of these strains have been send to the Deutsche Sammlung von Mikroorganismen und Zellkulturen GmbH (DSM) for an independent identification using comparisons of 16S ribosomal DNA sequences as described by Nielsen et al. (1994, FEMS Microbiol. Lett. 117, 61–65). On the basis of this sequence comparison the eight strains can be assigned to the genus Bacillus and are most related to *B.alcalophilus (DSM 485$^T$)*. The sequence comparison further shows that the eight strains fall into two groups. The first group is very similar or almost identical to DSM 8721 and comprises strains 1-16-2, 1-25-2, and 1-43-3 (CBS 670.93, 671.93, 672,93, respectively). The second group is most related to DSM 8718 and comprises strains 2-47-1, 2-M-1, 1-47-3 and 2-26-2 (CBS 666.93, 667.93, 669.93 and 673.93), respectively. The classification of the deposited strains into these two groups is confirmed by xylanase zymograms.

Surprisingly, we have found that the xylanases obtainable from the first group of strains, i.e. the strains most related to DSM 8721 (comprising 1-16-2, 1-25-2, and 1-43-3) show a superb performance in the bleaching of pulp. This performance is exemplified by the increased brightness of both soft-wood and hard-wood pulp when treated with the enzymes of the present invention and is most pronounced on softwood pulp. In this respect, the performance of the xylanases obtainable from most of the strains in the second group, i.e. the group related to DSM 8718, is much less, although the xylanases obtainable from strain 1.47.3. shows the best performance on hard-wood pulp as compared to the other strains. The increase in brightness obtained with the enzymes of the present invention is at least 1.0, expressed as Δ Final ISO Brightness over the non-enzymatically treated control pulp. Preferably the brightness increase in the case of soft-wood pulp is between 1.5 and 5.0, and in the case of hard-wood pulp between 1.2 and 3.0.

The present invention discloses enzymes having xylanase activity and having a considerable xylanase activity at pH 9 and at a temperature of about 70° C. Said enzymes are obtainable from the deposited strains. Said enzymes are also obtainable from mutants and variants of the deposited strains.

With the expression 'considerable activity' is meant that the enzymes of the present invention have at pH=9, 40% of the activity they possess at s pH=7, preferably this is 60%, more preferably about 80%. In a most preferred embodiment of the present invention the activity of the xylanase is higher at pH=9 than at pH=7.

The present invention also discloses a process for the production of subject xylanases, which can be developed using genetic engineering. As a first step the genes encoding the xylanases of the present invention can be cloned using λ-phage (expression-) vectors and *E.coli* host cells. Alternatively, PCR cloning using consensus primers designed on conserved domains may be used. On the basis of homology comparisons of numerous xylanases a distinction in different classes has been proposed (Gilkes et al., 1991, Microbiol. Rev. 55, 303–315). For each class specific conserved domains have been identified. Class F and class G xylanases can be identified based on this determination. DNA-fragments in between two conserved domains can be cloned using PCR. Full length clones can be obtained by inverse PCR or by hybridization cloning of gene libraries. Expression of some of the genes encoding the xylanases of the present invention in *E.coli* is shown to give an active protein. Said proteins are active at pH 9 at a temperature of 70° C.

After a first cloning step in *E.coli*, a xylanase gene can be transferred to a more preferred industrial expression host such as Bacillus or Streptomyces species, a filamentous fungus such as Aspergillus, or a yeast. High level expression and secretion obtainable in these host organisms allows accumulation of the xylanases of the invention in the fermentation medium from which they can subsequently be recovered.

The present invention further relates to a process for the preparation of xylanases obtainable from the deposited strains and having considerable activity at a pH of 9 at a temperature of 70° C. The process comprises cultivation of the deposited microorganisms or recombinant host microorganisms expressing genes encoding the xylanases of the present invention in a suitable medium, followed by recovery of the xylanases.

The enzymes of the present invention have been shown to have a considerable activity on oat spelt xylan and on birchwood xylan.

The enzymes of the present invention have further been tested for their bleaching activities. The enzyme preparations, xylanases, are capable of delignifying wood pulp at a temperature of at least 80° C. and a pH of at least 9. The expression "wood pulp" is to be interpreted broadly and is intended to comprise all kinds of lignocellulosic materials. The enzymes of the present invention can be used immediately after the oxygen delignifying step in the paper and pulp preparation process described above. Preferably, the enzymes are used before the oxygen delignifying step. In this step the lignin concentration is much higher therefore the effect of the application of the xylanase is much larger.

The enzymes of the present invention have been tested for their activity on both hardwood and softwood pulps. Apart from the kappa reduction, also the increase in brightness has been determined on two types of pulp, both soft-wood and hard-wood kraft pulp in ECF bleaching experiments. It follows that the increased brightness produced by the xylanases of the present invention would also allow to reduce the amount of bleaching chemicals while achieving the same brightness as obtained without the use of enzymes.

Furthermore, the inventions relates to the applications of the enzyme preparations of the invention, particularly to a process in which wood pulp is treated with said enzyme preparations according to the invention, and a wood pulp and a fluff pulp treated with the enzyme preparations according to the invention.

The invention further relates to paper, board and fluff pulp made from a wood pulp treated with the enzyme preparations according to the invention.

The enzyme preparations of the present invention have further been shown to have a low cellulase activity.

EXAMPLE 1

Isolation of Alkali- and Thermotolerant Xylanases
Samples
  Soil and water samples were collected in the environments of alkaline soda lakes in Kenya, East Africa.
Screening for xylanase producing microorganisms
  Two methods were applied for the isolation of xylanase-producing microorganisms:
i) The soil and water samples were suspended in 0.85% saline solution and directly used in the xylan-agar diffusion assay.

ii) The soil and water samples were incubated in a xylan containing liquid minimal medium or GAM-medium for 1 to 3 days at 45, 55 and 70° C. respectively. Cultures that showed bacterial growth were analyzed for xylanase activity using the xylan-agar diffusion assay.

Media

The minimal medium (pH 9.7) used in the xylan-agar diffusion assay and the enrichment procedure, consisted of $KNO_3$ 1%, Yeast extract (Difco) 0.1%, $KH_2PO_4$ 0.1%, $MgSO_4.7H_2O$ 0.02%, $Na_2CO_3$ 1%, NaCl 4% and a mixture (0.05% each) of four commercially available xylans [Xylan from oat spelts (Sigma X-0376), Xylan from birchwood (Sigma X-0502), Xylan from oat spelts (Serva 38500), Xylan from larchwood (ICN Biochemicals 103298)]. For solidification 1.5% agar is added.

The complex medium (GAM) used for enzyme production consisted of Peptone (Difco) 0.5%, Yeast extract (Difco) 0.5%, Glucose.$H_2O$ 1%, $KH_2PO_4$ 0.1%, $MgSO_4.7H_2O$ 0.02%, $Na_2CO_3$ 1%, NaCl 4%. The pH is adjusted to 9.5 with 4M HCl after which 1% Xylan (Serva) is added.

Xylan-agar diffusion assay

Cell suspensions in 0.85% saline solution were plated on Xylan containing minimal medium. After incubation for 1 to 3 days at 45 and 55° C. respectively, the strains that showed a clearing zone around the colony were isolated as potential xylanase producing microorganisms.

Strains that showed clearing zones in the agar diffusion assay were fermented in 25 ml GAM-medium in 100 ml shake flasks in an Incubator Shaker (New Brunswick Scientific, Edison, N.J., USA), at 250 r.p.m. at 45° C. for 72 hours. Xylanase activity was determined in the culture broth at pH 9 and 80° C. (Example 2).

Isolation of crude enzyme preparations

Shake flask fermentations were carried out in 2 l erlenmeyer flasks containing 500 ml GAM-medium. The flasks were incubated in an orbital incubator at 250 r.p.m. at 45° C. for 48 to 96 hours. The cells were separated from the culture liquid by centrifugation (8000 rpm). The cell-free culture liquid was concentrated by ultrafiltration, using an Amicon Stirred Cell Model 8400 with YM5 filter.

EXAMPLE 2

Characterization of Alkali- and Thermotolerant Xylanases

Analytical methods

Assays for xylanase activity are performed using modified procedures of the Sumner assay (J. Biol.Chem. 1921. 47 5–9).

Procedure 1

Xylanase activity on Oat Spelts xylan

A test tube is filled with 200 μl 4% Oat spelts xylan suspension, 600 μl aliquots of cell-free culture broth (Example 1) diluted in the appropiate buffer. The test tube is incubated in a waterbath for 15 minutes. After the incubation, 7.2 ml DNS (Dinitrosalicylic acid) reagent is added. The mixture is heated in a waterbath at 100° C. for 10 minutes. After heating the mixture the test tube is cooled on ice. The absorbance is measured at 575 nm. To eliminate the background absorbance of the enzyme samples a control experiment was executed as follows: a tube with substrate incubated under the same conditions as the test tube. After incubation 7.2 ml DNS and the enzyme preparation is added (in this order). One unit of xylanase (xU) activity is defined as the amount of enzyme producing 1 μmol of xylose from xylan equivalent determined as reducing sugar per minute.

Actual measuring conditions were pH 7, 9 and 70 and 80° C. The buffers were Phosphate pH 7 and Borate/KCl pH 9. The results are shown in table 1 as relative activity.

TABLE 1

Relative xylanase activities on Oat Spelts xylan
RELATIVE XYLANASE ACTIVITY ON OAT SPELTS XYLAN

| | strain | 70 ° C. | |
| --- | --- | --- | --- |
| Nr | number | pH 7 | pH 9 |
| 1 | 1-47-3 | 100 | 82 |
| 2 | 2-47-1 | 100 | 51 |
| 3 | 2-m-1 | 100 | 67 |
| 4 | 1-16-2 | 100 | 55 |
| 5 | 1-25-2 | 100 | 40 |
| 6 | 2-16-1 | 100 | 63 |
| 7 | 1-43-3 | 100 | 48 |
| 8 | 2-26-2 | 100 | 59 |

The values for pH9 in Table 1 represent the percentage of activity retained at pH9 relative to the activity at pH7 set at 100.

The strains indicated in Tables 1, 2 and 3 as 1 to 8 have been deposited under the following deposition numbers;

2-47-1=CBS 666.93, 2-m-1=CBS 667.93

2-16-1=CBS 668.93, 1-47-3=CBS 669.93

1-16-2=CBS 670.93, 1-25-2=CBS 671.93

1-43-3=CBS 672.93, 2-26-2=CBS 673.93

Procedure 2

Xylanase activity on Birchwood xylan

The same method as described in procedure 1 is used. Instead of a 4% Oat Spelts xylan suspension a 4% Birchwood xylan suspension is used. The test conditions were: pH 7 and 9 and 70 and 80° C., respectively. The results are shown in table 2.

TABLE 2

Relative xylanase activities on Birchwood xylan

| Nr | strain | pH 7 70° C. | pH 9 70° C. | pH 7 80° C. | pH 9 80° C. |
| --- | --- | --- | --- | --- | --- |
| 1 | 1-47-3 | 100 | 72 | 100 | 10 |
| 2 | 2-47-1 | 100 | 80 | 100 | 9 |
| 3 | 2-M-1 | 100 | 90 | 100 | 8 |
| 4 | 1-16-2 | 100 | 40 | 100 | 42 |
| 5 | 1-25-2 | 100 | 24 | 100 | 65 |
| 6 | 2-16-1 | 100 | 74 | 100 | 11 |
| 7 | 1-43-3 | 100 | 23 | 100 | 55 |
| 8 | 2-26-2 | 100 | 69 | 100 | 18 |

The values for pH9 in Table 2 represent the percentage of activity retained at pH9 relative to the activity at pH7 set at 100.

EXAMPLE 3

Deignification assay at 70° C. and 80° C.

Kappa assay

The kappa assay's were performed according to the TAPPI T236 protocol with some modifications. The enzyme solution was added at a dose of 10×U/g pulp (based on Oat spelts xylan for the pulp nb 1 and based Birchwood xylan for pulps 2 and 3) (dry weight) and incubated for 2 hours at pH 9, 70 and 80° C. The control, was pulp incubated for the same period under the same conditions without enzyme addition. Tree different pulps were used:

1] Kraft softwood pulp

2] Kraft softwood pulp after oxygen delignification

3] Kraft hardwood pulp after oxygen delignification

Pulp properties (nb 2 and 3):

|  | Hardwood Birch 80% | Softwood spruce, 20% pine |
| --- | --- | --- |
| Brightness, % ISO | 50.8 | 35.8 |
| Kappa number | 11.0 | 16.7 |
| Viscosity, dm³/kg | 979 | 1003 |
| Calcium, ppm | 1900 | 2600 |
| Copper, ppm | 0.3 | 0.6 |
| Iron, ppm | 5.1 | 11 |
| Magnesium, ppm | 210 | 270 |
| Manganese, ppm | 25 | 70 |

The difference between the kappanumber with enzyme addition and the kappanumber without enzyme addition is called the kappa reduction and is a value for delignification. The kappa reductions are shown in table 3A.

TABLE 3A

Kappa reductions at pH 9 and 70 °C. and 80 °C.

| Nr | Strain Number | pH 9 70° C. Softwood kraft pulp (nb 1) kappa red | pH 9 70° C. Softwood O2 delig (nb 2) kappa red | pH 9 80° C. Hardwood O2 delig (nb 3) kappa red |
| --- | --- | --- | --- | --- |
| 1 | 1-47-3 | 1.7 | 0.3 |  |
| 2 | 2-47-1 | 2 |  |  |
| 3 | 2-M-1 | 2 |  |  |
| 4 | 1-16-2 | 1.8 |  |  |
| 5 | 1-25-2 | 1.6 | 1.1 | 0.5 |
| 6 | 2-16-1 | 0.4 |  |  |
| 7 | 1-43-3 | 1.1 | 1.2 | 1 |
| 8 | 2-26-2 | 0.5 |  |  | blanks were not determined.

Delignification assay at 60° C.
Kappa assay

The kappa assay's were performed according to the Tappi T236 protocol with some modifications. The enzyme solution was added at a dose of 10×U/g pulp (based on birchwood xylan) (dry weight) and incubated for 2 hours at pH 9, 60° C. The control, was pulp incubated for the same period under the same conditions without enzyme addition. Two different pulps were used:

Kraft hardwood pulp after oxygen delignification (nb 2).

Kraft softwood pulp after oxygen delignification (nb 4).

Pulp properties (nb 2 and 4)

|  | Hardwood Birch 80% | Softwood |
| --- | --- | --- |
| Brightness, % ISO | 50.8 | 40.0 |
| Kappa number | 11.0 | 10.1 |
| Viscosity, dm³/kg | 979 | 940 |
| Calcium, ppm | 1900 | 1800 |
| Copper, ppm | 0.3 | 0.3 |
| Iron, ppm | 5.1 | 5.2 |
| Magnesium, ppm | 210 | 250 |
| Manganese, ppm | 25 | 35 |

The difference between the kappanumber with enzyme addition and the kappanumber without enzyme addition is called the kappa reduction and value for delignification. The kappa reductions are shown in table 3B.

TABLE 3B

Kappa reductions at pH 9 and 60° C.

| Nr | Strain number | Softwood O2 delig kappa red | Hardwood O2 delig kappa red. |
| --- | --- | --- | --- |
| 1 | 1-47-3 | 0.0 |  |
| 2 | 2-47-1 | 0.9 |  |
| 3 | 2-M-1 | 0.5 | 0.6 |
| 4 | 1-16-2 | 1.1 | 0.7 |
| 5 | 1-25-2 | 0.9 | 0.2 |
| 6 | 2-16-1 | 0.7 | 0.2 |
| 7 | 1-43-3 | 1.1 |  |
| 8 | 2-26-2 | 0.7 |  |

EXAMPLE 4

Cellulase activity

Assay's for cellulase activity were performed using a modified procedure of the PAHBAH (parahydroxybenzoicacid hydrazide) assay (Anal. Biochem. 1972. 47: 273–279)

0.9 ml 0.5% CMC (carboxymethylcellulose) is incubated with 0.1 ml diluted enzyme preparation and incubated for 60 minutes at pH 9 and 70° C. after the incubation 3 ml PAHBAH reagent (10 ml 5% PAHBAH in 0.5M HCl was mixed with 40 ml 0.5M NaOH=PAHBAH reagent) is added and the reaction mixture is heated for 5 minutes at 100° C. After cooling on ice the absorbance is measured at 420 nm. To eliminate the background absorbance of the enzyme samples a control experiment was executed as follows: the CMC was incubated for 30 minutes at pH 9, 70° C. and the enzyme solution is added after adding of the PAHBAH reagent. One cellulase unit (cU) is defined as the quantity of enzyme necessary to produce one $\mu$Mol glucose per minute (using CMC as substrate) and is related to the xylanase activity. All strains tested showed a cellulase activity less than 10 mU CMCase per unit of xylanase.

EXAMPLE 5

Cloning of xylanase genes and fragments thereof

Chromosomal DNA was isolated from strains mentioned in Example 2 according to methods described (Maniatis et al, Cold Spring Harbor Laboratory Press, 1989). Genomic libraries were prepared for each of these selected strains using the ZAP Express® cloning system available from Stratagene. The host/vector system was used according to the instructions of the supplier (Catalog # 239212, Jun. 30, 1993). For construction either partial Sau3A digest ligated into the BamH1 site or randomly sheared DNA supplied with EcoR1 linkers ligated into the EcoR1 site were used.

Recombinant phages were transformed into plasmid vectors as recommended by the supplier. These plasmid vectors were tested for expression of xylanase using RBB xylan indicator plates.

Positive colonies were isolated and tested for production of xylanase using the following medium:

Production medium:

4×L B C:

20 g yeast extract 40 g Bacto trypton 10 g NaCl 4 g casaminoacids fill up to 1 liter with demineralized water add 0.25 ml antifoam and sterilize 20' at 120° C. Colonies are grown during 24 hr at 30° C. under vigourous shaking.

The enzyme was isolated using a heat shock method (10' at 65° C.) to lyse the cells. Xylanase activity was measured as described above. The results of the tests of individual clones are summarized in Table 4.

TABLE 4

Xylanase activities of cloned xylanases expressed in E. coli.

| Strain | Clone | Production level (U/ml) |
|---|---|---|
| 1-47-3 | KEX101 | 0.6 |
|  | KEX106 | 23.7 |
|  | KEX107 | 17 |
| 2-M-1 | KEX202 | <0.2 |
|  | KEX203 | 4.0 |
| 1-43-3 | KEX301 | 40 |
|  | KEX303 | 1.1 |
|  | KEX304 | 1.8 |
| 2-26-2 | KEX401 | 12 |
|  | KEX402 | 12 |
|  | KEX403 | 43 |
|  | KEX404 | 33 |
|  | KEX405 | <0.2 |
|  | KEX406 | 17 |
|  | KEX407 | 110 |
|  | KEX408 | 0.8 |
|  | KEX409 | 36 |

It can be concluded that all clones produce xylanase. Although the variability in production level might be due to cloning of partial gene fragments, it most probably can be regarded as a reflection of the diversity of xylanase genes present within the inserts.

EXAMPLE 6

Characterization of selected xylanase encoding inserts

The DNA insert of xylanase producing clones can be characterized by DNA sequencing. The insert of KEX106 was analysed and a gene encoding the alkalitolerant xylanase was identified. The DNA sequence of the gene is shown in SEQ ID NO 1.

A comparison of the amino acid sequence of the encoding protein (SEQ ID NO 2) revealed an homology to xylanase protein sequences, i.e. 93% [Hamamoto et al., 1987, Agric. Biol Chem., 51, 953–955].

The amino acid sequence of xylanases of the present invention can therefore share an identity with the amino acid sequence of SEQ ID NO 2 of higher than 93%, preferably the identity is at least 95%, more preferably the identity is at least 98%, and most preferably more than 99%.

EXAMPLE 7

Identification and cloning of internal fragments of genes encoding alkalitolerant xylanases As an alternative method to the screening of gene libraries we have worked out a method based on PCR cloning. On the basis of a comparison of numerous xylanase sequences we have designed consensus oligonucleotide primers encompassing conserved sequence boxes. Two types of primers have been designed. One set of primers is for the F-type of xylanase and one set is for the G-type of xylanases.

The following consensus primers have been constructed:

FA: 5' CAC ACT/G CTT/G GTT/G TGG CA 3': forward primer, consensus box 1 (SEQ ID NO 3)

FB: 5' CAT ACT/G TTT/G GTT TGG CA 3': forward primer, consensus box 1 (SEQ ID NO 4)

FR: 5' TC/AG TTT/G ACC/A ACG/A TCC CA 3': reverse primer, consensus box 2 (SEQ ID NO 5)

Primers FA and FB bind to the same consensus box, but due to slight differences in the nucleotide sequence they exhibit complementary specificity.

PCR conditions were as follows: [94° C., 1 min], [50° C., 1 min] and [72° C., 1 min] for 30 cycles. Fragments originating from amplification with F-type primers were purified on agarose gel and subcdoned. Subsequently the DNA sequence was determined.

$G_{AF}$: 5' GAA/G TAT/C TAT/C ATT/C/A GTN GA: forward primer, consensus box 1 (SEQ ID NO 6)

$G_{BF}$: 5' GAA/G TAT/C TAT/C GTN GTN GA: forward primer, consensus box 1 (SEQ ID NO 8)

$G_{AR}$: 5' CG/TN ACN GAC CAA/G TA: reverse primer consensus box 2 (SEQ ID NO 7)

$G_{BR}$: 5' CG/TN ACA/G CTC CAA/G TA: reverse primer consensus box 2 (SEQ ID NO 9)

$G_{CR}$: 5' CCR CTR CTK TGR TAN CCY TC: reverse primer consensus box 3 (SEQ ID NO 10)

PCR conditions were as follows: [94° C., 1 min], [40° C., 1 min] and [72° C., 1 min] for 30 cycles.

The first PCR with G-primers was performed with primers constructed on box 1 and box 3. The resulting mixture of fragments of different sizes were subsequently purified from agarose gel (250–340 bp) and subjected to a second round of PCR, now using primers from box 1 and box 2. Unique fragments were amplified and subcloned. The blunt-end repair of the PCR fragments was performed in the PCR mix by adding 0.5 mM ATP (Boehringer Mannheim), 10 u T4 DNA kinase (BRL), 1 u T4 DNA polymerase (BRL) and incubation at 37° C. for 1 hour. The mixture was purified using the PCR extraction kit from Qiagen. The fragment was ligated into the pUC18×SmaI (ClAP) vector obtained from Appligene according to Maniatis. E. coli HB101laqlq was transformed with the ligation mixture using electroporation. The DNA sequence of a number of individual clones was determined.

From the analysis it has become apparent that the selected strains harbor several different xylanase genes, some of which may be cloned by the F-type consensus primers and other which may be cloned by the G-type of primers. As an example several different internal xylanase fragments originating from strains 1-43-3, 1-47-3, 1-M-1, 2-26-2 (all F-type) and 1-43-3 and 1-25-2 (all G-type) are depicted in the sequence listings (see Table 5).

TABLE 5

| Strain | Consensus primers used | Sequence listing |
|---|---|---|
| 1-43-3 | F-type | SEQ ID NO 11 |
| 1-47-3 | F-type | SEQ ID NO 12 |
| 2-26-2 | F-type | SEQ ID NO 13 |
| 2-M-1 | F-type | SEQ ID NO 14 |
| 1-25-2 | G1-type | SEQ ID NO 15 |
| 1-43-3 | G1-type | SEQ ID NO 16 |
| 1-43-3 | G2-type | SEQ ID NO 17 |

The cloned internal fragment are subsequently used as a specific probe to isolated the cloned gene fragments from the lambdaZAP gene library using stringent hybridisation conditions. All cloned genes can be isolated using this method.

The method is especially advantageous for those genes that do not express well from their native gene regulatory signals in E.coli, since these genes would escape from detection in the method described in example 5. Using subcloning methods and DNA sequence analysis the complete genes encoding the various alkalitolerant xylanases can be isolated and equipped with expression signals for production in E.coli.

EXAMPLE 8
Further characterization of xylanase clones

With the aid of both the consensus primers and specific primers a further characterization of the clones mentioned in example 5 was performed. It became apparent that there is a clustering of xylanase genes on several of the cloned inserts. On the basis of this inventory single genes were subcdoned in expression vectors for both E. coli and Bacillus subtilis. Expression of monocomponent xylanases was obtained upon transformation into E.coli and Bacillus respectively. The Bacillus expression system was based on the PlugBug® technology [ref 1]

EXAMPLE 9
Characterization of selected G-type xylanase encoding insert

The insert of clone KEX301 was analysed and an open reading frame encoding a G-type xylanase was identified. The sequence of this ORF is given in SEQ ID NO 18 and the derived amino acid sequence for the xylanase in SEQ ID NO 19. A search for homologous genes within the EMBL database (release 39, version 2) showed that the sequence of G1 xylanase is unique. No DNA homology of more than 68% was detected. Also the protein sequence was compared to the database sequences. The closest homology (72%) was found with a xynY xylanase sequence (Yu et al. 1993, J. Microbiol. Biotechnol. 3, 139–145).

The amino acid sequence of xylanases of the present invention can therefore share an identity with the amino acid sequence of SEQ ID NO 19 of at least 72%, preferably the identity is at least 80%, more preferably the identity is at least 90%, still more preferably the identity is at least 95%, and most preferably more than 99%.

ref1: Quax, W. J. et al, 1993, in Industrial Microorganisms: Basic and Applied Molecular Genetics, ASM, Washington D.C., p143.

EXAMPLE 10
Pulp bleaching experiments with supernatants from deposited strains All experiments were elemental chlorine free (ECF) bleaching with a XwDED bleach sequence. Enzyme treatments on pulp were for two ours at pH 9.0 and 65° C. To ensure proper temperature throughout the experiment the pulp has been heated in the microwave to 65° C. before adding enzyme. Experiments were run at a pulp consistency of 10%, which was adjusted by adding pH adjusted tap water. A summary of the ECF bleaching data for xylanase containing culture supernatants of the deposited strains is shown in Table 6.

Table 6. Brightness increase expresses as Δ Final ISO Brightness over the non-enzymatically treated control for the supernatants of the deposited strains and for the reference Cartazyme GT 630 (Sandoz).

TABLE 6

Brightness increase expresses as Δ Final ISO Brightness over the non-enzymatically treated control for the supernatants of the deposited strains and for the reference Cartazyme GT 630 (Sandoz).

| Strain/Enzyme | Softwood | Hardwood |
|---|---|---|
| 1.43.3 | 3.55 | 1.45 |
| 1.47.3 | 1.45 | 1.99 |
| 2.47.1 | 1.8 | 1.55 |
| 1.25.2 | 3.15 | 1.45 |
| 2.M.1 | 0 | 0.4 |

TABLE 6-continued

Brightness increase expresses as Δ Final ISO Brightness over the non-enzymatically treated control for the supernatants of the deposited strains and for the reference Cartazyme GT 630 (Sandoz).

| Strain/Enzyme | Softwood | Hardwood |
|---|---|---|
| 1.16.2 | 1.55 | 0.5 |
| 2.26.2 | 0 | 0.9 |
| GT 630 | 0 | 0 |

Before each bleaching experiment every enzyme containing supernatant was assayed for xylanase activity at pH 9.0, 65° C. In the bleaching experiments 2 xylanase units per gram of oven dried pulp were used for each supernatant. Supernatant activities were determined the same day the enzyme bleaching stage was run.

EXAMPLE 11
Pulp bleaching with cloned xylanase genes expressed in E.coli

Xylanases obtained from three of the E.coli clones expressing cloned xylanase genes obtained from the deposited strains were tested in pulp bleaching experiments as described in Example 10. The E.coli clones were cultured as described in Example 5. Recombinant enzyme was isolated from the E.coli bacteria in one of three ways:

1. Whole lysate

In this case, the whole cell culture (cells+spent growth medium) was harvested. Cells were disrupted by sonication followed by heat at 65° C. for 10 minutes. The lysates were then clarified by centrifugation.

2. Cell pellet

Cells were separated from spent medium by centrifugation. Cell pellets were resuspended at 10 ml/g wet weight in 50 mM Tris/HCl, pH 7.0 buffer. The cell suspension was then sonicated and heated as described for "whole lysate".

3 Culture supernatant

Spent growth medium was separated from whole cells by centrifugation. The clarified medium was then diafiltered (tangential flow, 10,000 MWCO membrane) to reduce the total volume and exchange the liquid 50 mM Tris/HCl, pH 7.0 buffer.

The results of the bleaching experiments are shown in Table 7.

TABLE 7

Pulp bleaching with cloned xylanase genes expressed in E. coli

| Parental strain | Clone # | source of enzyme | Δ Final ISO Brightness* Soft-wood | Hard-wood |
|---|---|---|---|---|
| 1-47-3 | KEX106 | whole lysate | decrease | decrease |
| 1-43-3 | KEX301 | whole lysate | 3.2 | n.d.** |
|  |  | cell pellet | 3.4 | 0.7 |
|  |  | cell pellet | n.d. | 1.0 |
|  |  | culture sup. | 3.6 | 1.5 |
| 1-43-3 | KEX303 | cell pellet | 3.2 | 1.6 |
|  |  | culture sup. | n.d. | 1.0 |

*over non-enzymatically treated control
**n.d. = not determined

EXAMPLE 12
Identification of the deposited strains

Most of these strains have been send to the Deutsche Sammlung von Mikroorganismen und Zellkulturen GmbH (DSM) for an independent identification using comparisons of 16S ribosomal DNA sequences as described by Nielsen et al. (1994, FEMS Microbiol. Lett. 117, 61–65). Seciicaly, strains 2-47-1; 2-M-1; 2-16-1; 1-47-3; 1-16-2; 1-25-2; 1-43-3; and 2-26-2 were deposited on Dec. 23, 1993 and have deposit numbers CBS666.93; CBS667.93; CBS668.93; CBS669.93; CBS670.93; CBS671.93; CBS672.93; and CBS673.93; respectively. These deposits were made under the terms of the Budapest Treaty and upon issuance of a patent on this application, all restrictions imposed by the depositor on availability to the public of the deposited material will be irrevocably removed. The results of this identification are provided in Table 8. On the basis of this sequence comparison the eight strains can be assigned to the genus Bacillus and among the known Bacilli, they are most related to *B.alcalophilus* (DSM 485$^T$).

The sequence comparison further shows that the eight strains fall into two groups. The first group is very similar or almost identical to DSM 8721 and comprises strains 1-16-2, 1-25-2, and 1-43-3 (CBS 670.93, 671.93, 672,93, respectively). The second group is most related to DSM 8718 and comprises strains 2-47-1, 2-M-1, 1-47-3 and 2-26-2 (CBS 666.93, 667.93, 669.93 and 673.93), respectively.

The xylanases of the invention are preferably obtainable from the first group of strains, i.e. the strains most related to DSM 8721 (comprising 1-16-2, 1-25-2, and 1-43-3). The xylanases of the present invention are therefore obtainable from Bacillus strains of which the 16S ribosomal DNA sequence shares at least 92% identity with strain DSM 8721, preferably the identity is at least 93.3%, more preferably at least 96.6%, still more preferably at least 99%, and in the most preferred embodiment the identity is 100%.

TABLE 8

16S rDNA sequence similarities of the deposited strains to some alkaliphilic Bacilli

| Strain | 1 | 2 | 3 | 4 | 5 | 6 | 7 | 8 | 9 | 10 | 11 |
|---|---|---|---|---|---|---|---|---|---|---|---|
| 1. 1-9A-1(93-509) | — | | | | | | | | | | |
| 2. 1-43-3(93-510) | 99.2 | — | | | | | | | | | |
| 3. 2-47-1(93-511) | 89.4 | 88.6 | — | | | | | | | | |
| 4. 2-26-2(93-512) | 89.5 | 88.9 | 99.6 | — | | | | | | | |
| 5. 1-25-2(93-513) | 100.0 | 98.6 | 89.3 | 89.3 | — | | | | | | |
| 6. 1-47-3(93-514) | 89.6 | 89.7 | 99.9 | 99.5 | 89.7 | — | | | | | |
| 7. 1-16-2(93-515) | 100.0 | 99.2 | 89.5 | 89.5 | 100.0 | 89.8 | — | | | | |
| 8. 2-M-1(93-516) | 89.6 | 89.5 | 99.9 | 99.8 | 89.5 | 99.7 | 89.7 | — | | | |
| 9. *B. alcalophilus* | 91.3 | 90.7 | 95.8 | 96.1 | 91.6 | 95.6 | 91.4 | 95.8 | — | | |
| 10 *B. colinii* | 88.0 | 87.4 | 92.4 | 92.1 | 87.2 | 92.0 | 88.0 | 92.0 | 93.4 | — | |
| 11. DSM 8714 | 89.6 | 88.6 | 92.6 | 92.2 | 89.3 | 92.5 | 89.7 | 92.4 | 94.9 | 91.9 | — |
| 12. DSM 8715 | 90.4 | 89.4 | 94.4 | 94.3 | 90.6 | 94.3 | 90.5 | 94.3 | 96.4 | 94.0 | 94.8 |
| 13. DSM 8716 | 89.6 | 88.7 | 93.3 | 92.8 | 89.6 | 93.0 | 89.8 | 92.9 | 95.0 | 92.0 | 96.0 |
| 14. DSM 8717 | 90.3 | 89.4 | 93.7 | 93.4 | 89.6 | 93.3 | 90.4 | 93.5 | 95.6 | 93.1 | 96.8 |
| 15. DSM 8718 | 88.8 | 88.0 | 98.9 | 99.3 | 89.5 | 99.0 | 88.9 | 99.1 | 96.3 | 93.7 | 93.6 |
| 16. DSM 8719 | 87.9 | 87.0 | 92.8 | 92.6 | 87.2 | 92.5 | 97.8 | 92.6 | 93.0 | 97.2 | 90.7 |
| 17. DSM 8720 | 95.6 | 94.6 | 92.5 | 92.4 | 95.6 | 92.5 | 95.6 | 92.5 | 93.3 | 91.7 | 90.9 |
| 18. DSM 8721 | 100.0 | 99.4 | 90.6 | 90.2 | 100.0 | 90.5 | 100.0 | 90.2 | 93.2 | 91.1 | 91.4 |
| 19. DSM 8722 | 90.0 | 89.1 | 92.3 | 92.1 | 90.3 | 92.0 | 90.1 | 92.1 | 94.7 | 92.1 | 94.6 |
| 20. DSM 8723 | 87.5 | 86.7 | 93.3 | 92.8 | 86.8 | 92.9 | 87.5 | 93.0 | 93.3 | 97.6 | 91.3 |
| 21. DSM 8724 | 91.3 | 90.3 | 95.7 | 96.1 | 91.7 | 95.6 | 91.4 | 95.8 | 99.9 | 93.3 | 94.8 |
| 22. DSM 8725 | 89.6 | 89.2 | 94.6 | 94.3 | 90.0 | 94.3 | 89.7 | 94.6 | 98.1 | 93.1 | 94.4 |
| 23. *B. subtilis* | 89.2 | 88.3 | 91.9 | 91.7 | 89.9 | 91.9 | 89.2 | 91.7 | 92.6 | 93.9 | 91.4 |

| Strain | 12 | 13 | 14 | 15 | 16 | 17 | 18 | 19 | 20 | 21 | 22 | 23 |
|---|---|---|---|---|---|---|---|---|---|---|---|---|
| 1. 1-9A-1(93-509) | | | | | | | | | | | | |
| 2. 1-43-3(93-510) | | | | | | | | | | | | |
| 3. 2-47-1(93-511) | | | | | | | | | | | | |
| 4. 2-26-2(93-512) | | | | | | | | | | | | |
| 5. 1-25-2(93-513) | | | | | | | | | | | | |
| 6. 1-47-3(93-514) | | | | | | | | | | | | |
| 7. 1-16-2(93-515) | | | | | | | | | | | | |
| 8. 2-M-1(93-516) | | | | | | | | | | | | |
| 9. *B. alcalophilus* | | | | | | | | | | | | |
| 10 *B. colinii* | | | | | | | | | | | | |
| 11. DSM 8714 | | | | | | | | | | | | |
| 12. DSM 8715 | — | | | | | | | | | | | |
| 13. DSM 8716 | 94.8 | — | | | | | | | | | | |
| 14. DSM 8717 | 94.2 | 96.1 | — | | | | | | | | | |
| 15. DSM 8718 | 96.0 | 94.0 | 93.8 | — | | | | | | | | |
| 16. DSM 8719 | 92.8 | 91.7 | 92.2 | 93.5 | — | | | | | | | |
| 17. DSM 8720 | 93.7 | 91.5 | 91.6 | 93.0 | 92.1 | — | | | | | | |
| 18. DSM 8721 | 93.3 | 91.9 | 91.7 | 92.3 | 91.0 | 96.6 | — | | | | | |
| 19. DSM 8722 | 94.8 | 94.4 | 94.4 | 94.0 | 91.3 | 92.1 | 92.1 | — | | | | |
| 20. DSM 8723 | 93.1 | 92.6 | 92.9 | 93.8 | 98.4 | 92.0 | 90.8 | 91.4 | — | | | |
| 21. DSM 8724 | 96.2 | 95.0 | 95.5 | 96.2 | 92.9 | 93.3 | 93.2 | 94.6 | 93.2 | — | | |
| 22. DSM 8725 | 95.9 | 94.8 | 94.8 | 95.4 | 92.4 | 93.0 | 92.2 | 94.5 | 92.8 | 90.1 | — | |
| 23. *B. subtilis* | 94.1 | 92.7 | 91.5 | 93.5 | 93.3 | 91.5 | 91.5 | 91.6 | 93.7 | 92.5 | 92.9 | |

What is claimed is:

1. An isolated and purified xylanase having activity at pH 9.0 and at a temperature of 70° C. which xylanase produces at least a 1% increase in ISO brightness of soft wood pulp over non-enzymatically treated pulp in an ECF pulp bleaching process conducted at pH 9.0 and 65° C., wherein said xylanase is selected from the group consisting of
   a) that contained in the cell culture supernatant of a single strain of a xylanase producing microorganism;
   b) that contained in a culture of cells modified recombinantly to produce said xylanase; and
   c) that added to and contained in said ECF pulp bleaching process mixture and wherein said xylanase producing microorganism is Bacillus DSM 8721 and said xylanase shares more than 72% identity with the amino acid sequence as listed in SEQ ID No: 19; or said xylanase shares more than 98% identity with the amino acid sequence as listed in SEQ ID NO: 2.

2. An isolated and purified xylanase having activity at pH 9.0 and at a temperature of 70° C. which xylanase produces at least a 1% increase in ISO brightness of soft wood pulp over non-enzymatically treated pulp in an ECF pulp bleaching process conducted at pH 9.0 and 65° C., wherein said xylanase is selected from the group consisting of
   a) that contained in the cell culture supernatant of a single strain of a xylanase producing organism;
   b) that contained in a culture of cells modified recombinantly to produce said xylanase; and
   c) that added to and contained in said ECF pulp bleach process mixture and wherein said microorganism is selected from the group consisting of the strains deposited under the deposition numbers: CBS 666.93, 669.93 and 637.93 and said xylanase shares more than 72% identity with the amino acid sequence as listed in SEQ ID No: 19; or said xylanase shares more than 98% identity with the amino acid sequence as listed in SEQ ID NO: 2.

3. An isolated DNA sequence encoding a xylanase according to claim 1 or 2.

4. A vector capable of transforming a microbial host cell wherein said vector comprises a DNA sequence according to claim 3.

5. The vector of claim 4 wherein said DNA sequence is operably linked to expression signals that ensure the expression of the DNA sequence in the microbial host.

6. A microbial host which contains a vector according to claim 4.

7. The microbial host of claim 6 wherein said microbial host expresses the DNA sequence.

8. A process for the preparation of a xylanase useful in wood processing which method comprises cultivating the microbial host of claim 7 in a suitable medium, followed by recovering said xylanase.

9. A process for degradation of xylan which process comprises contacting said xylan with a xylanase according to claim 1 or 2.

10. A process for delignifying wood pulp which process comprises contacting said wood pulp with a xylanase according to claim 1 or 2.

11. A process for the bleaching of pulp which process comprises contacting said pulp with a xylanase according to claim 1 or 2.

12. The xylanase of claim 1 or 2 which shares more than 99% identity with the amino acid sequence as listed in SEQ ID NO:2.

* * * * *